United States Patent
Nielsen

(10) Patent No.: US 8,880,357 B2
(45) Date of Patent: Nov. 4, 2014

(54) APPARATUS FOR ESTIMATING A RESONANT FREQUENCY OF A WIND TURBINE TOWER

(75) Inventor: Rasmus Nielsen, Brande (DK)

(73) Assignee: kk-electronic A/S, Ikast (DK)

( * ) Notice: Subject to any disclaimer, the term of this patent is extended or adjusted under 35 U.S.C. 154(b) by 0 days.

(21) Appl. No.: 13/993,228

(22) PCT Filed: Dec. 15, 2010

(86) PCT No.: PCT/DK2010/050340
§ 371 (c)(1),
(2), (4) Date: Aug. 21, 2013

(87) PCT Pub. No.: WO2012/079574
PCT Pub. Date: Jun. 21, 2012

(65) Prior Publication Data
US 2014/0012516 A1    Jan. 9, 2014

(51) Int. Cl.
*G01B 3/00* (2006.01)
*G01H 13/00* (2006.01)
*G01N 29/12* (2006.01)
*F03D 11/04* (2006.01)

(52) U.S. Cl.
CPC .............. *G01N 29/12* (2013.01); *G01H 13/00* (2013.01); *F05B 2270/404* (2013.01); *Y02E 10/728* (2013.01); *F05B 2260/96* (2013.01); *F05B 2260/80* (2013.01); *F03D 11/04* (2013.01)
USPC ......................................................... 702/33

(58) Field of Classification Search
None
See application file for complete search history.

(56) References Cited

U.S. PATENT DOCUMENTS

| 7,317,260 | B2 * | 1/2008 | Wilson ............................ 290/44 |
| 2010/0111693 | A1 * | 5/2010 | Wilson ............................... 416/1 |
| 2010/0289266 | A1 | 11/2010 | Wortmann et al. |
| 2012/0010852 | A1 * | 1/2012 | Winkelmann et al. ........ 702/179 |

FOREIGN PATENT DOCUMENTS

| EP | 1643122 A2 | 4/2006 |
| EP | 2103915 A1 | 9/2009 |
| WO | 2008081232 A1 | 7/2008 |

* cited by examiner

*Primary Examiner* — Aditya Bhat
(74) *Attorney, Agent, or Firm* — Gifford, Krass, Sprinkle, Anderson & Citkowski, P.C.

(57) ABSTRACT

The invention regards an apparatus for estimating a resonant frequency of a wind turbine tower, comprising a measuring module adapted for measuring acceleration values of the wind turbine tower wherein the acceleration values represent acceleration of the wind turbine tower, a filter module adapted for receiving the measured acceleration values, the filter module comprises a variable filter wherein the variable filter is adapted to attenuate frequencies in a band hereby attenuating frequencies for an output of the filter module, an adaptive algorithm module comprising an adaptive algorithm wherein the adaptive algorithm module is adapted for communicating with the filter module and wherein the adaptive algorithm is adapted to minimize the energy of the output of the filter module by adjusting the band of attenuated frequencies, a resonant frequency estimating module adapted for estimating the resonant frequency of a wind turbine tower based on the attenuated frequencies.

19 Claims, 7 Drawing Sheets

APPARATUS FOR ESTIMATING A RESONANT FREQUENCY OF A WIND TURBINE TOWER

CROSS-REFERENCE TO RELATED APPLICATIONS

This application is the U.S. National Phase of PCT/DK2010/050340 filed Dec. 15, 2010.

FIELD OF THE INVENTION

The invention relates to an apparatus for estimating a resonant frequency of a wind turbine tower comprising a measuring module adapted for measuring acceleration values of the wind turbine tower wherein the acceleration values represent acceleration of the wind turbine tower, as well as a method of determining a resonant frequency of a wind turbine tower, comprising receiving acceleration measurement values of an acceleration of a wind turbine tower.

BACKGROUND OF THE INVENTION

A wind turbine generates electrical energy by converting the energy in the wind. The electrical energy can be supplied to the electric power transmission network.

It is known in the art that a wind turbine system is prone to changes in the wind which cause the tower to oscillate back and forth and/or sideways or sometimes in circle-like oscillations. These oscillations reduce the lifetime of the tower and other parts of the wind turbine system. Additionally, the oscillations increase if they match the tower resonant frequency, which reduce the lifetime even more.

It is known in the art that these oscillations can be determined by measuring the acceleration of the wind turbine tower.

US patent application 2009/0230682 A1 discloses an apparatus for determining a resonant frequency of a wind turbine tower. The apparatus includes a processing unit configured to receive an acceleration measurement value, and a memory configured to store a series of acceleration measurement values. The processing unit includes a Fourier transform module configured to calculate a spectral vector based on calculating a convolution-based fast Fourier transform of the series of acceleration measurement values. A resonant frequency calculation module calculates the tower resonant frequency based on the calculated spectral vector.

SUMMARY OF THE INVENTION

Considering the prior art described above, it is an object of the present invention to enable the estimation of the resonant frequency of a wind turbine tower on the basis of the signal energy from measurement of the tower acceleration.

The object can be achieved by means of an apparatus for estimating a resonant frequency of a wind turbine tower, comprising a measuring module adapted for measuring acceleration values of the wind turbine tower wherein the acceleration values represent acceleration of the wind turbine tower, a filter module adapted for receiving the measured acceleration values, the filter module comprises a variable filter wherein the variable filter is adapted to attenuate frequencies in a band hereby attenuating frequencies for an output of the filter module, an adaptive algorithm module comprising an adaptive algorithm wherein the adaptive algorithm module is adapted for communicating with the filter module and wherein the adaptive algorithm is adapted to minimise the energy of the output of the filter module by adjusting the band of attenuated frequencies, a resonant frequency estimating module adapted for estimating the resonant frequency of a wind turbine tower based on the attenuated frequencies.

Thus, it is possible to obtain an estimate of the resonant frequency, also called the natural oscillation frequency, or simply the natural frequency, of a wind turbine tower in a simple and cost effective way. The information of the resonant frequency could be used to hinder that other parts of the wind turbine system, for example the rotors, oscillate with the same frequency. Hereby, increasing the life time of the wind turbine system and/or reducing the risk of failure of the wind turbine system. The apparatus according to the invention can be designed as a compact unit and can thus be incorporated into the wind turbine system e.g. in the tower or in the nacelle and can be accessible via a wireless system if needed. The resonant frequency is a characteristic of wind turbine tower dependent, among other things, on the height and weight of the nacelle, tower and rotor and the material composition of the parts of the wind turbine.

The measuring of the acceleration values can, for example, be a continuous measurement or a plurality of discrete measurements that are received by the filter module. The measured acceleration values can also be stored for any given time before the filter module receives them.

The band of attenuated frequencies should be understood as a range or interval of frequencies that are attenuated. The filter will normally not attenuate all frequencies with the same magnitude.

In an embodiment the acceleration values are measured in a plane perpendicular to the tower, preferably parallel to the rotor axle and/or perpendicular to the rotor axle. The acceleration measured in the plane perpendicular to the tower and parallel to the rotor axle is also known as the fore-aft direction. The acceleration measured in the plane perpendicular to the tower and perpendicular to the rotor axle is also known as the sideward direction.

As the person skilled in the art will acknowledge, in the entire present document, the terms "parallel" and "perpendicular" are to be understood as including a certain amount of derivation from its actual precise orientation. For example in some wind turbine systems, the rotor axle is inclined upwards by a small angle in relation to the horizontal direction in order to prevent that the blades come into contact with the tower during high wind pressures as it bends the blades in direction towards the tower.

Preferably, the measuring module comprises an accelerometer. This can be a single- and/or a multi-axis model detecting the magnitude and direction of the acceleration of the wind turbine tower as a vector quantity. An accelerometer is also known as a g-sensor. The accelerometer can be positioned in the nacelle.

In an embodiment, the variable filter is a band-stop filter. A band-stop filter is also known as a notch filter, band limit filter or band-elimination filter. It is a filter that allows most frequencies to pass unaltered but attenuates frequencies in a specific band to low levels. The range of the stop-band can be less that 0.2 Hz within a −3 dB bandwidth, preferably less than 0.15 Hz, more preferably less than 0.1 Hz.

In an embodiment, the variable filter comprises an IIR filter. The function of an IIR (Infinite impulse response) filter is non-zero over infinite length of time, and is thus a suitable filter for the present embodiment.

In an embodiment, the adaptive algorithm module receives an input from the output of the variable filter and/or an input of the acceleration values of the wind turbine tower. These inputs can be used in optimising the algorithm, aid the algorithm to ensure that the resonant frequency is in the attenuated band and prevent the algorithm from drifting away from the resonant frequency once it has found it.

Preferably, the adaptive algorithm is an adaptive LMS algorithm or an adaptive RLS algorithm as they can adapt an IIR type filter or a FIR (Finite impulse response) type filter.

In an embodiment, the resonant frequency is estimated as the centre frequency of the attenuated band. This is a relatively simple way of estimating the centre frequency and does not require any additional calculation. Thus, resonant frequency estimating module can be made relatively simple and cost effective.

Preferably, the resonant frequency estimating module is communicating with the adaptive algorithm module. Hence, data generated in the adaptive algorithm module, for example the data on the attenuated band, can be received by the resonant frequency estimating module without the risk of interference during the process.

In an embodiment, the apparatus further comprises a sensor that is able to establish the frequency of the rotor rotation. Knowledge of the rotor frequency of the rotor rotation can be compared with the resonant frequency of a wind turbine tower in order to establish if there is an undesired correlation between the two.

Preferably, the filter module further comprises a 1P filter that attenuates the 1P-oscillation frequency based on the established frequency of the rotor rotation. When the rotor rotates, it generates an oscillation which is mainly caused by unbalance in the rotor or the blades; this frequency is called the 1P frequency. It can be ensured that the 1P-frequency is not mistaken to be the resonant frequency by attenuating the 1P-frequency.

Preferably, the filter module further comprises a 3P filter that attenuates the 3P-oscillation frequency based on the established frequency of the rotor rotation. The wind speed over the entire rotor of a wind turbine system normally differs so that the wind speed increases with an increasing height over the ground. This phenomenon is also known as wind sheer. The oscillations in the wind turbine tower that are caused by this effect are called 3P oscillations. To prevent the apparatus from erroneously determining the resonant frequency of a wind turbine tower to be the 3P frequency, the 3P-frequency can be attenuated.

It should be noted that the filter module, the adaptive algorithm module and the resonant frequency estimating module can be integrated into one unit or module having multiple functionalities. Further it should be noted that not all the modules of the present invention needs to be positioned in or near the wind turbine.

The present invention also regards a method of determining a resonant frequency of a wind turbine tower, comprising receiving acceleration measurement values of an acceleration of a wind turbine tower, forwarding the acceleration measurement values to a variable filter which attenuates a frequency band by use of an adaptive algorithm, adapting the adaptive algorithm to minimise the energy of the output of the variable filter by adjusting the band of attenuated frequencies, determining the resonant frequency on the basis of the attenuated frequencies.

Using the method provides a reliable and cost effective way of determining the resonant frequency of a wind turbine tower, which can be used to ensure that no other parts of the tower oscillate with the same frequency. Contributing to a longer life time of the wind turbine tower.

DESCRIPTION OF THE DRAWINGS

The invention will in the following be described in greater detail with reference to the accompanying drawings.

DETAILED DESCRIPTION OF THE INVENTION

Figure 1:
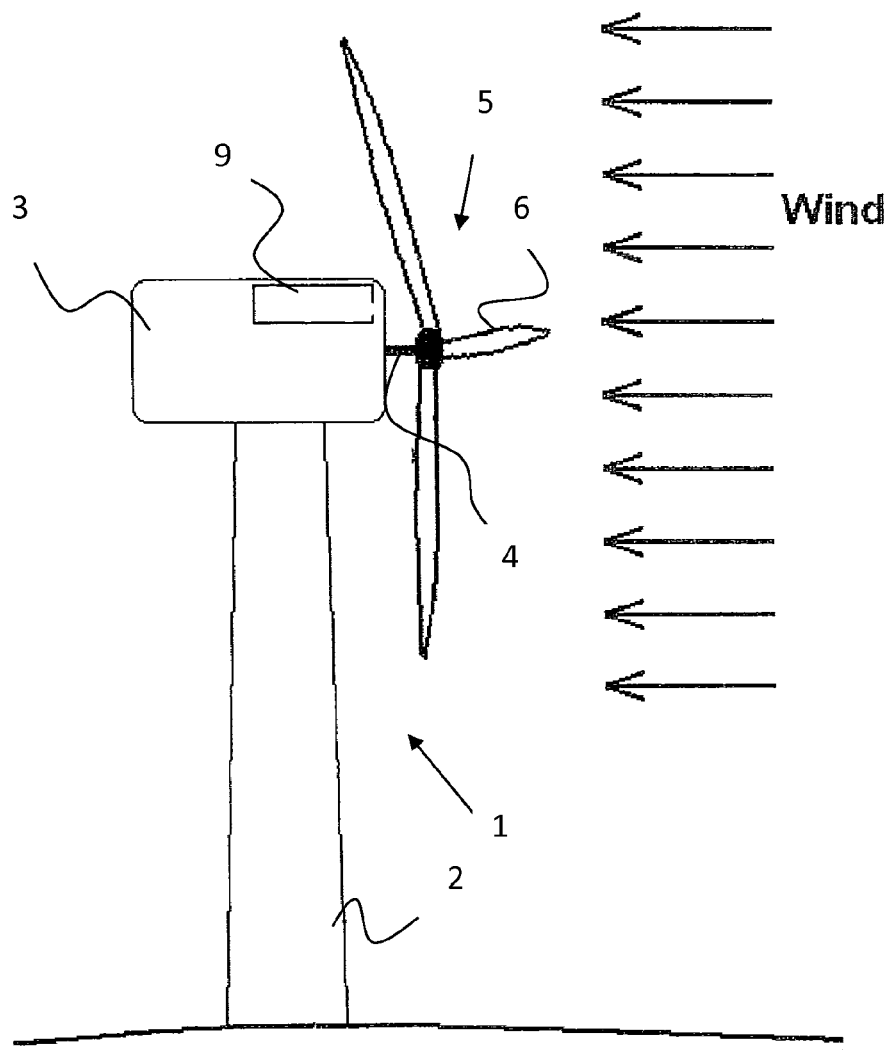
FIG. 1 a schematic side view of a wind turbine.

FIG. 1 shows a wind turbine 1 with a tower 2 and a nacelle 3. The axle 4 has a rotor 5 with three blades 6, as is common for modern wind turbines although the wind turbine 1 could have any number of blades. When wind is present, it stimulates the rotor 5 which then starts to rotate. The rotational energy taken from the wind energy will be converted to electrical energy in a generator in the nacelle 3. The wind turbine 1 can then transmit the electricity to the utility grid.

Figure 2:
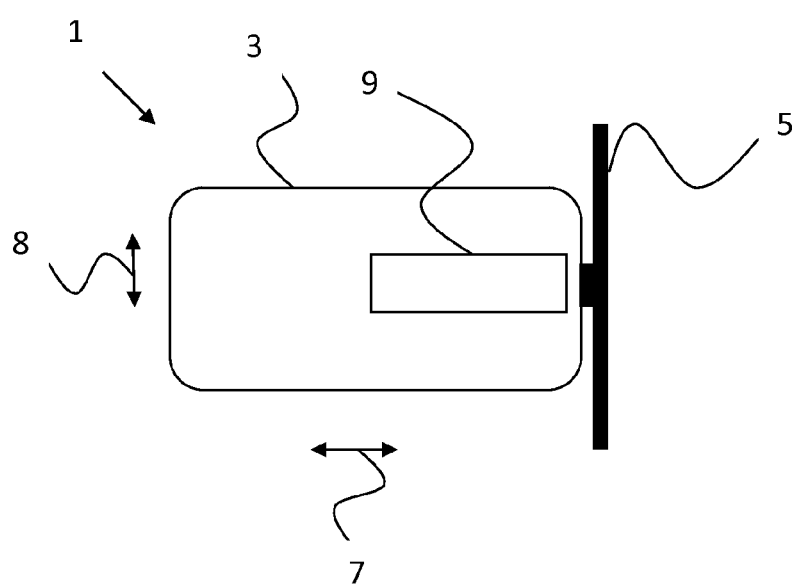
FIG. 2 a schematic top view of a wind turbine.

FIG. 2 shows the wind turbine from above, where the nacelle 3 and the rotor 5 can be seen. During operation the wind turbine 1 can start to oscillate. There are normally three major contributors to the oscillation of a wind turbine. The rotation of the rotor generates a frequency component corresponding to the rotor speed. The frequency is called the 1P-frequency. The 1P-frequency is usually caused by an unbalance between the blades for instance if their weights differ or difference in their pitch calibration. Due to the use of three blades, there is also generated a frequency component corresponding to three times the rotor speed. This frequency is called the 3P-frequency. This is generated because the speed of the wind is larger at an increased height. This generates a large force on the blade when it is pointing upwards compared to the other blades thereby introducing a frequency that is three times the rotor speed. Additionally, there is the resonant frequency of the tower, this is the natural oscillation frequency of the wind turbine and is dependent on the tower characteristics like height and total weight of the tower, nacelle, foundation and rotor, and on the material used for the wind turbine. This frequency remains generally constant even though the rotor speed is changing. The present invention provides an apparatus and a method for determining the resonant frequency of the tower.

The oscillation can have a fore-aft component and a sideways component. The fore-aft component is illustrated by the arrows 7 and the sideways component is illustrated with the arrows 8. The wind turbine 1 has a measuring module 9 having a accelerometer which is positioned in the nacelle, that can measure the oscillations of the wind turbine 1. These measurements can be used to determine the resonant frequency of the tower 2, this can be done by using the sideways and/or the fore-aft acceleration measurement and/or by combining the measurements.

Figure 3:
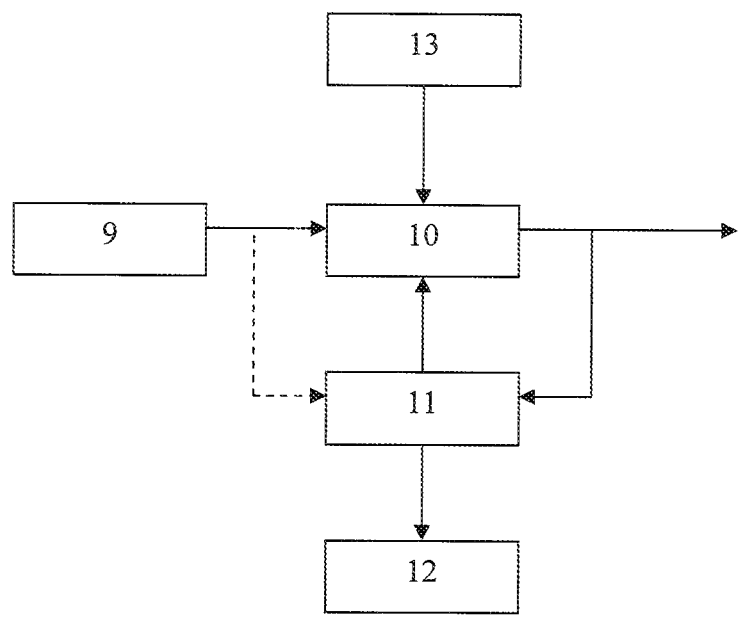
FIG. 3 a schematic view of an aspect of the invention.

FIG. 3 is a sketch of an embodiment of the invention that is able to estimate the natural frequency of a wind turbine tower. A measuring module 9 has an accelerometer which establishes acceleration values of the tower 2 by continuously measuring the acceleration. During the development of the present invention, the inventor has realised that it is possible to estimate the natural frequency of a wind turbine tower from the signal received from the sideways oscillations of the tower alone. This is because the natural oscillation seams to be more distinct in that signal compared to the fore-aft signal.

The signal from the measuring module 9 is transmitted to the filter module 10 that attenuates a band of frequencies established by the adaptive algorithm module 11. The filtered signal output of the filter module 10 is transmitted to the adaptive algorithm module 11. Additionally, the adaptive algorithm module 11 can receive an unaltered signal directly from the accelerometer 9, in the present embodiment only the signal from the filter module 10 is used.

The filtered signal from the filter module 10 can be used to determine the performance of the apparatus for estimating a resonant frequency of a wind turbine tower. By evaluating the output of the filter module 10 with the filter on and with the filter off the effect of the filter module 10 can be established.

The adaptive algorithm module 11 establishes the frequency that has the highest energy contribution to the signal and communicates that frequency to the filter module 10. The filter module 10 attenuates a band or interval of frequencies centred at that frequency. The adaptive algorithm module 11 also communicates the frequency to the estimating module 12.

By using the established frequency, the estimating module 12 estimates the natural frequency of the tower. The established frequency can in some cases, drift over time but will stay close to the true resonant frequency of the tower, statistical methods can be used to evaluate the changes in the established frequency to find a estimate of the natural resonant frequency of the wind turbine tower. In the present embodiment, the natural frequency is estimated as the frequency established by the adaptive algorithm module 11.

In order to ensure that the adaptive algorithm module 11 does not accidentally find the 1P or the 3P frequency, these frequencies can be removed from the signal transmitted to the module 11. This can be done by the use of a rotor rotation module 13 that establishes the rotational speed of the rotor and thus its rotor frequency. Then, the frequencies in a band around the rotor frequency are attenuated to remove the 1P frequency and the band around three times the rotor frequency is attenuated which will remove the 3P frequency from the signal. Attenuating the 1P and the 3P frequency can be done with the knowledge of the rotor rotational frequency, thus, without the need of an analysis of the signal. Having removed the 1P and the 3P frequency from the signal, the natural frequency of the tower will be the most significant frequency. In the embodiment shown, the removal of the 1P and the 3P frequencies is done in the filter module 10 but it can be done anywhere, for example be a part of the adaptive algorithm. Some wind turbines are designed to have a constant rotor speed in which case, the 1P and 3P filter can be a simple static filter attenuating frequencies around the predefined rotor frequency.

In the present embodiment, an adaptive LMS algorithm in the adaptive algorithm module 11 is used to minimise the signal energy by the use of a band-stop filter in the filter module 10. The band-stop filter is implemented using an IIR (Infinite impulse response) filter. The band-stop filter will dampen a narrow band of frequencies around a centre frequency which will be the most significant frequency, established by the adaptive algorithm.

Figure 6:
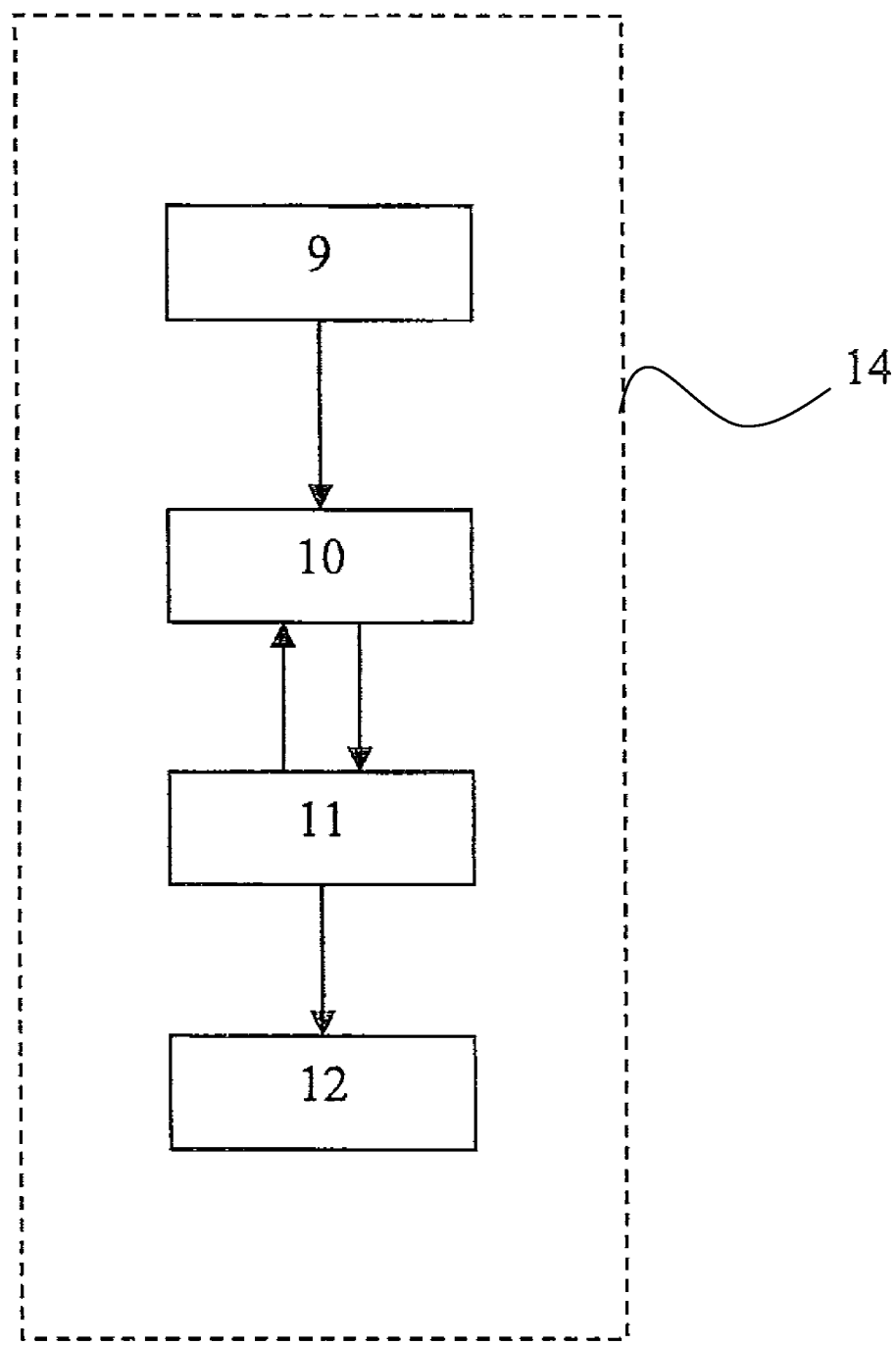

FIG. 6 shows an apparatus 14 for estimating a resonant frequency of a wind turbine tower. The apparatus 14 is a simpler embodiment than the schematic view of the invention shown in FIG. 3. For consistency the same reference numbers are used for the same objects as the previous embodiment. The apparatus 14 comprises a measuring module 9, wherein a accelerometer establishes acceleration values. These values are forwarded to the filter module 10 which attenuates frequencies in a band around a centre frequency. The centre frequency is established by the adaptive algorithm module 11 by receiving the filtered signal from the filter module 10 and then minimise the energy in the signal by adjusting the centre frequency. The centre frequency is then forwarded to the filter module 10. The resonant frequency estimating module 12 receives the data regarding the centre frequency and then establishes the resonant frequency of 1 wind turbine tower.

In the following, the adaptive LMS algorithm that can be used in the adaptive algorithm module 11 is described.

The adaptive LMS algorithm can be based on recursively or updating the estimate of the resonant frequency of a wind turbine tower by use of the derivative of a cost function. The cost function can be defined as the difference between the desired filter response and the actual filter response, as shown in equation 1.

$$J(n) = \frac{1}{2}e^2(n) = \frac{1}{2}(d(n) - y(n))^2, \quad \text{Equation 1}$$

where d(n) is the desired response, y(n) is the actual response and e(n) is the error signal.

The update equation used to find an estimate can be based on the derivative of the cost function and a step size ($\mu$) as shown in equation 2.

$$\hat{w}(n+1) = \hat{w}(n) - \mu \cdot \frac{\partial J(n)}{\partial \hat{w}(n)}, \quad \text{Equation 2}$$

where $\hat{w}(n)$ is a vector containing the parameters to optimize.

As stability is not guaranteed when using an IIR filter, the implementation has to ensure the stability. This can be done by choosing a filter structure where the poles are placed within the unit circle in the z-domain. The implementation of the IIR filter stop-band of the present embodiment is shown in equation 3.

$$H(z) = \frac{1 - 2 \cdot \cos(\phi) \cdot z^{-1} + z^{-2}}{1 - 2 \cdot r \cdot \cos(\phi) \cdot z^{-1} + r^2 \cdot z^{-2}}, \quad \text{Equation 3}$$

In this filter implementation the parameter r is giving the filter characteristic as a compromise between the width and damping at the band-step while the parameter $\phi$ gives the centre frequency in [rad] found with respect to the sample rate using equation 4.

$$\phi = \frac{2 \cdot \pi \cdot f}{F_S}, \quad \text{Equation 4}$$

where f is the frequency in [Hz], $\phi$ is the frequency in [rad] and $F_S$ is the sample rate in [Hz].

Figure 4:
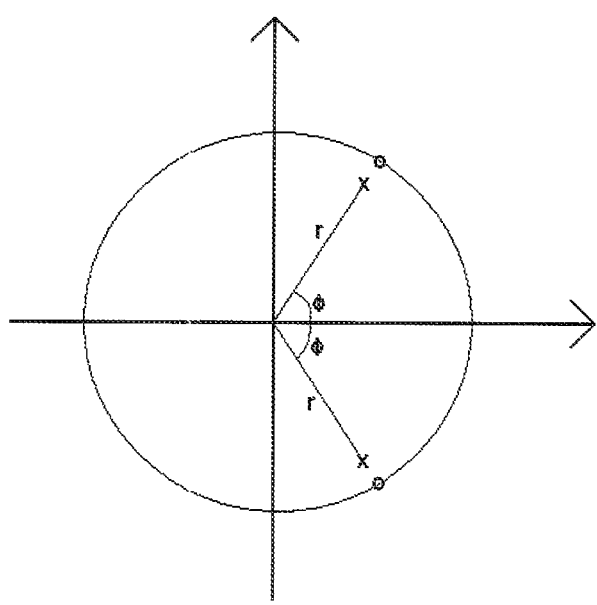
FIG. 4 a schematic view of a pole-zero placement for the band-stop filter implementation in the z-domain.

The filter implementation in the z-domain places a complex conjugate zero pair on the unit circle and a complex conjugate pole pair within the unit circle as illustrated on FIG. 4.

Figure 5:
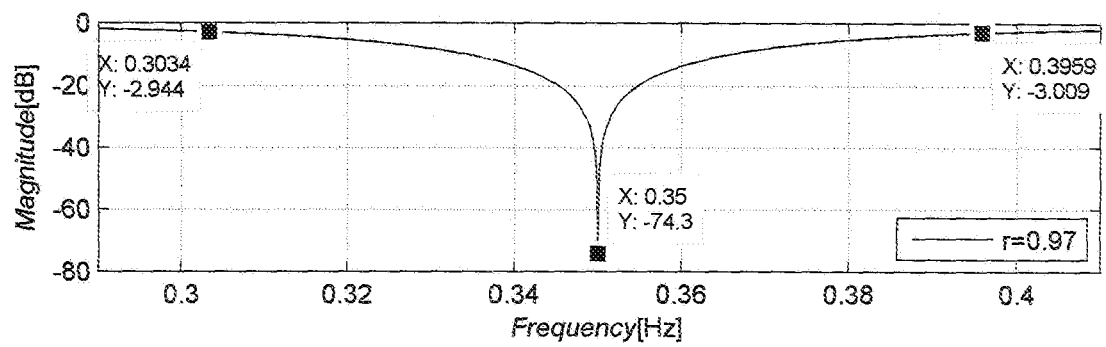
FIG. 5 a schematic view of the effect of changing the IIR filter
FIG. 6 a schematic view of an apparatus according to the invention.

The parameter r determines the frequency characteristics of the filter. In FIG. 5, the filter of the present embodiment is shown. The centre frequency is 0.35 Hz and r=0.97 which makes the band-stop span from approximately 0.3 Hz to 0.4 Hz. The chosen parameter makes the filter commonly adapt successfully to the most significant frequency within ±0.5 Hz of the given centre frequency. However, the performance will vary according to the SNR (Signal-to-noise ratio) and characteristics of the excitation signal.

The implementation of the chosen IIR filter is shown in equation 5, expressed as a function in the time domain.

$$y(n) = x(n) - 2 \cdot \cos(\phi) \cdot x(n-1) + x(n-2) + 2 \cdot r \cdot \cos(\phi) \cdot y(n-1) - r^2 \cdot y(n-2),$$ Equation 5

By implementing the filter and applying the LMS algorithm, the centre frequency of the IIR filter can be optimised in order to minimize the energy of the filter response. Equation 5 can be used as the general expression of the update equation for an adaptive LMS algorithm applied to an IIR filter. The equation is simplified to one equation as only one parameter is to be optimized, namely $\phi$, accordingly:

$$\phi(n+1) = \phi(n) - \mu \cdot \frac{\partial J(n)}{\partial \phi(n)},$$ Equation 6

$\phi$ is consistent with the frequency of the IIR filter shown in equation 5 and as mentioned, it is the only parameter to be estimated.

The partial derivative of the cost function is found in equation 7 using the definition of the cost function in equation 1.

$$\frac{\partial J(n)}{\partial \phi(n)} = \frac{1}{2} \cdot \frac{\partial e(n)^2}{\partial \phi(n)} \Leftrightarrow$$ Equation 7

$$= e(n) \cdot \frac{\partial e(n)}{\partial \phi(n)} \Leftrightarrow$$

$$= (-y(n)) \cdot \frac{\partial (-y(n))}{\partial \phi(n)}$$

The implementation of the differentiation can be done by dividing the difference in y(n) with the difference in $\phi(n)$ as shown in Equation 8.

$$\frac{\partial y(n)}{\partial \phi(n)} = \frac{y(n) - y(n-1)}{\phi(n) - \phi(n-1)}$$ Equation 8

The differentiation in this case is problematic as the difference from $\phi(n)$ to $\phi(n-1)$ might be zero which yields division by zero in the derivation. To avoid this issue, the partial derivative of the filter output equation is found and used to calculate the derivative.

Finding the partial derivative of the filter output can be done by considering the implementation of the filter written in equation 5. The partial derivative of the filter output with respect to $\phi$ is found in equation 9.

$$\frac{\partial y(n)}{\partial \phi(n)} = \frac{\partial}{\partial \phi(n)} (x(n) - 2 \cdot \cos(\phi) \cdot x(n-1) + x(n-2) + 2 \cdot r \cdot \cos(\phi) \cdot y(n-1) - r^2 \cdot y(n-2)) \Leftrightarrow$$ Equation 9

$$= \frac{\partial}{\partial \phi(n)} (-2 \cdot \cos(\phi) \cdot x(n-1) + 2 \cdot r \cdot \cos(\phi) \cdot y(n-1) - r^2 \cdot y(n-2)) \Leftrightarrow$$

$$= 2 \cdot \sin(\phi) \cdot x(n-1) + 2 \cdot r \cdot \cos(\phi) \cdot \frac{\partial y(n-1)}{\partial \phi(n)} -$$

-continued $$2 \cdot r \cdot \sin(\phi) \cdot y(n-1) - r^2 \cdot \frac{\partial y(n-2)}{\partial \phi(n)}$$

The found partial derivative depends on partial derivatives of y(n−1) with respect to $\phi(n)$. The partial derivative can be calculated recursively assuming the change from $\phi(n)$ to $\phi(n-1)$ is small enough making the two assumptions in equation 10 valid.

$$\frac{\partial y(n-1)}{\partial \phi(n)} \approx \frac{\partial y(n-1)}{\partial \phi(n-1)}$$ Equation 10

$$\frac{\partial y(n-2)}{\partial \phi(n)} \approx \frac{\partial y(n-2)}{\partial \phi(n-2)}$$

The assumptions in equation 10 imply that the change of the frequency parameter is small for each step. This is true for small values of $\mu$ as shown in equation 11.

$$\phi(n) \approx \phi(n-1) \approx \phi(n-2) \Leftrightarrow$$ Equation 11

$$\phi(n) \approx \phi(n) + \mu \cdot \frac{\partial J(n)}{\partial \phi(n)} \approx \phi(n) + \mu \cdot \frac{\partial J(n)}{\partial \phi(n)} + \mu \cdot \frac{\partial J(n+1)}{\partial \phi(n+1)}$$

The assumptions simplify equation 9 to the expression shown in equation 12.

$$\frac{\partial y(n)}{\partial \phi(n)} = 2 \cdot \sin(\phi) \cdot x(n-1) + 2 \cdot r \cdot \cos(\phi) \cdot \frac{\partial y(n-1)}{\partial \phi(n-1)} -$$ Equation 12

$$2 \cdot r \cdot \sin(\phi) \cdot y(n-1) - r^2 \cdot \frac{\partial y(n-2)}{\partial \phi(n-2)}$$

The partial derivative of the filter can be found and the update equation is thereby given as equation 13.

$$\phi(n+1) = \phi(n) + \mu \cdot y(n) \cdot \frac{\partial y(n)}{\partial \phi(n)},$$ Equation 13 where y(n) is found from equation 12.

With the response of the IIR filter and the update equation specified the algorithm used in the present embodiment is now presented. It is quite simple and requires only a few calculations during every single iteration. An initial guess can be introduced to help the algorithm converge faster and make the likelihood of errors smaller. The initial guess in the present case is chosen to be 0.

The steps in the adaptive LMS IIR filter can be expressed as:

1) Find the initial condition for the filter.
2) Iteratively calculate the following steps.
   a. Calculate the filter output y(n).
   b. Calculate the filter derivative $$\frac{\partial y(n)}{\partial \phi(n)}.$$

c. Calculate the new angle $\phi(n+1)$ using equation 13
   d. Output the angle after each iteration.

The computational complexity of the adaptive LMS algorithm according to the embodiment can be seen in Table 1 and based implementation of the equations described above.

TABLE 1

Computational complexity for the adaptive LMS algorithm on an IIR filter

| Steps | Multiplications | Additions | Sine/Cosine | Division |
|---|---|---|---|---|
| A | 7 | 4 | 2 | 0 |
| b | 10 | 3 | 3 | 0 |
| C | 3 | 2 | 0 | 1 |
| D | — | — | — | — |
| Total | 20 | 9 | 5 | 1 |

As can be seen in the table, the complexity of the adaptive LMS algorithm according to the present embodiment of the invention is relatively simple.

The IIR filter contains two parameters where the parameter r has been described above and visualized in FIG. 5 which shows the change in filter characteristics when changing the parameter r. The filter parameter $\phi$ changes the centre frequency of the filter and this is the adaptively estimated parameter.

The step size $\mu$ can be chosen to be above the highest expected amplitudes of the filter response to guarantee the stability. In the present embodiment, non-normalized adaptive LMS algorithm is chosen which allows the algorithm to take larger steps when the oscillations are stronger making the algorithm adapt stronger when the signal holds more energy. The step size can, for example, be chosen to be $\mu=1e-4$ or $\mu=1e-5$.

The present embodiment as explained above uses an adaptive algorithm to minimise the signal energy of measured acceleration values from a wind turbine by applying a variable filter.

Figure 7:
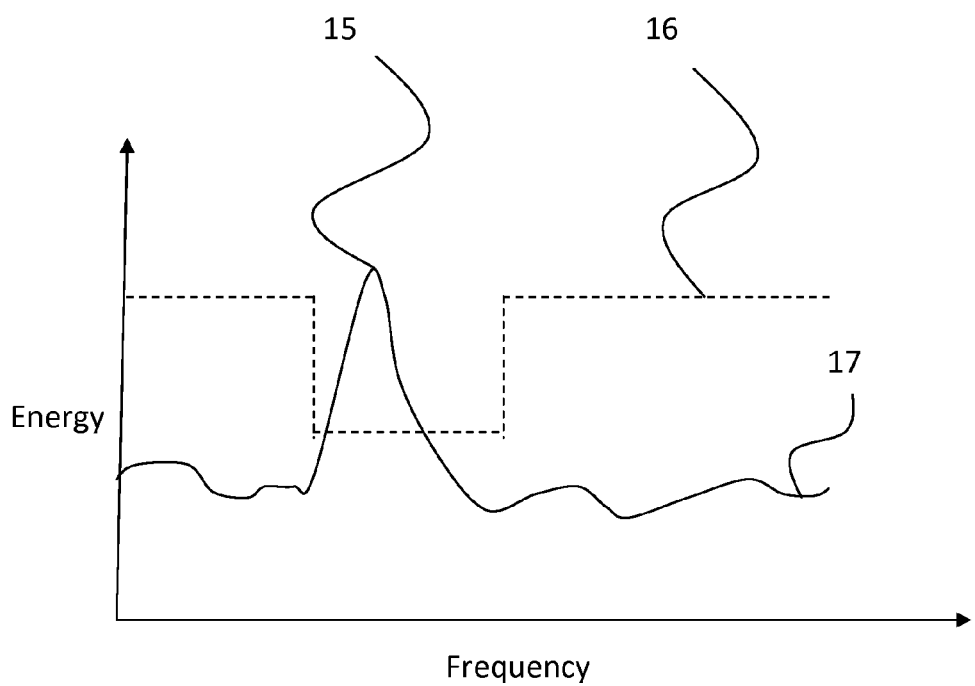
FIG. 7 a schematic view of graph illustrating aspects of the invention.

FIG. 7 is a graphic illustration of the invention in a frequency-energy diagram. With a graph 17 showing the frequencies of the measurements of the accelerometer 9. The resonant frequency of the wind turbine tower 2 can be seen as the peak 15. This resonant peak 15 can be the resonant frequency. The adaptive filter applied to the signal is shown as the filter graph 16. As can be seen the filter attenuates the frequencies around the peak 15 and hereby attenuating the resonant frequency.

The invention is described above with reference to several embodiments. However, it is realised that other suitable solutions may be provided without departing from the scope of the invention as defined in the accompanying claims.

REFERENCE LIST

1 wind turbine
2 tower
3 nacelle
4 axle
5 rotor
6 blades
7 fore-aft
8 sideways
9 measuring module
10 filter module
11 adaptive algorithm module
12 resonant frequency estimating module
13 rotor rotation module
14 apparatus for estimating a resonant frequency of a wind turbine tower
15 resonant peak
16 filter graph
17 frequency graph

The invention claimed is:

1. Apparatus for estimating a resonant frequency of a wind turbine tower, comprising
   a measuring module adapted for measuring acceleration values of the wind turbine tower wherein the acceleration values represent acceleration of the wind turbine tower,
   a filter module adapted for receiving the measured acceleration values, the filter module comprises a variable filter wherein the variable filter is adapted to attenuate frequencies in a band hereby attenuating frequencies for an output of the filter module,
   an adaptive algorithm module comprising an adaptive algorithm wherein the adaptive algorithm module is adapted for communicating with the filter module and wherein the adaptive algorithm is adapted to minimise the energy of the output of the filter module during operation of the wind turbine by adjusting the band of attenuated frequencies of the variable filter,
   a resonant frequency estimating module adapted for estimating the resonant frequency of a wind turbine tower based on the attenuated frequencies.

2. Apparatus according to claim 1, wherein acceleration values are measured in a plane perpendicular to the tower.

3. Apparatus according to claim 1, wherein the measuring module comprises an accelerometer.

4. Apparatus according to claim 1, wherein the variable filter is a band-stop filter.

5. Apparatus according to claim 4, wherein the range of the stop-band is less that 0.2 Hz within a −3 dB bandwidth.

6. Apparatus according to claim 1, wherein the variable filter comprises an IIR filter, preferably the filter is based on the expression in the z-domain, $$H(z) = \frac{1 - 2 \cdot \cos(\phi) \cdot z^{-1} + z^{-2}}{1 - 2 \cdot r \cdot \cos(\phi) \cdot z^{-1} + r^2 \cdot z^{-2}},$$

where $\phi$ is the center frequency of the attenuated frequency.

7. Apparatus according to claim 1, wherein the adaptive algorithm module receives an input from the output of the variable filter and/or an input of the acceleration values of the wind turbine tower.

8. Apparatus according to claim 1, wherein the adaptive algorithm is an adaptive LMS algorithm or an adaptive RLS algorithm.

9. Apparatus according to claim 1, wherein the adaptive algorithm is an adaptive LMS algorithm based on the minimising of a cost function, expressed as $$J(n) = \frac{1}{2}e^2(n) = \frac{1}{2}(d(n) - y(n))^2,$$

wherein $d(n)$ is the desired response, $y(n)$ is the actual response and $e(n)$ is the error signal.

10. Apparatus according to claim 9 wherein the adaptive algorithm determines a center frequency, by use of the updating equation, $$\phi(n+1) = \phi(n) - \mu \cdot \frac{\partial J(n)}{\partial \phi(n)},$$

wherein $\phi$ is the center frequency of the attenuating band, $\mu$ is the step size and $J(n)$ is the cost function.

11. Apparatus according to claim 1, wherein the resonant frequency is estimated as the center frequency of the attenuated band.

12. Apparatus according to claim 1, wherein the resonant frequency estimating module is communicating with the adaptive algorithm module.

13. Apparatus according to claim 1, further comprising a sensor that is able to establish the frequency of the rotor rotation.

14. Apparatus according claim 13, wherein the filter module further comprises a 1P filter, that attenuates the 1P-oscillation frequency based on the established frequency of the rotor rotation.

15. Apparatus according claim 13, wherein the filter module further comprises a 3P filter, that attenuates the 3P-oscillation frequency based on the established frequency of the rotor rotation.

16. Method of determining a resonant frequency of a wind turbine tower, comprising
receiving acceleration measurement values of an acceleration of a wind turbine tower, by means of a measuring module,
forwarding the acceleration measurement values to a filter module which comprises a variable filter which attenuates a frequency band by use of an adaptive algorithm,
adapting the adaptive algorithm to minimise the energy of the output of the variable filter during operation of the wind turbine by adjusting the band of attenuated frequencies of the variable filter,
determining the resonant frequency on the basis of the attenuated frequencies by means of a resonant frequency estimating module.

17. Method according to claim 16, wherein the variable filter is a band-stop filter.

18. Method according to claim 16, wherein the algorithm is, at least partly, based on values of the acceleration after the variable filter has been applied.

19. Method according to claim 16, wherein the resonant frequency is determined to be the center frequency of the band of attenuated frequencies.

\* \* \* \* \*